(12) United States Patent
Kota et al.

(10) Patent No.: US 8,993,722 B2
(45) Date of Patent: Mar. 31, 2015

(54) PROCESS FOR THE PREPARATION GLATIRAMER ACETATE (COPOLYMER-1)

(75) Inventors: Satyanarayana Kota, Hyderabad (IN); Venkateswarlu Tallapaneni, Hyderabad (IN); Bhujanga rao Adibhatla Kali Satya, Hyderabad (IN); Nannapaneni Venkaiah Chowdary, Hyderabad (IN)

(73) Assignee: Natco Pharma Limited, Banjara Hills, Hyderabad (IN)

( * ) Notice: Subject to any disclaimer, the term of this patent is extended or adjusted under 35 U.S.C. 154(b) by 829 days.

(21) Appl. No.: 12/671,082

(22) PCT Filed: Sep. 24, 2007

(86) PCT No.: PCT/IN2007/000432
§ 371 (c)(1),
(2), (4) Date: Sep. 1, 2010

(87) PCT Pub. No.: WO2009/016643
PCT Pub. Date: Feb. 5, 2009

(65) Prior Publication Data
US 2010/0324265 A1    Dec. 23, 2010

(30) Foreign Application Priority Data
Jul. 31, 2007 (IN) .......................... 1673/CHE/2007

(51) Int. Cl.
*A61K 38/04* (2006.01)
*C07K 5/00* (2006.01)
*C07K 7/00* (2006.01)
*C07K 16/00* (2006.01)
*C07K 17/00* (2006.01)
*C07K 14/00* (2006.01)
*C08G 69/10* (2006.01)

(52) U.S. Cl.
CPC .............. *C07K 14/001* (2013.01); *C08G 69/10* (2013.01)
USPC ........................................................ 530/330

(58) Field of Classification Search
None
See application file for complete search history.

(56) References Cited

U.S. PATENT DOCUMENTS

| | | |
|---|---|---|
| 3,849,550 A | 11/1974 | Teitelbaum et al. |
| 5,800,808 A | 9/1998 | Konfino et al. |
| 5,981,589 A | 11/1999 | Konfino et al. |
| 6,048,898 A | 4/2000 | Konfino et al. |
| 6,054,430 A | 4/2000 | Konfino et al. |
| 6,342,476 B1 | 1/2002 | Konfino et al. |
| 6,362,161 B1 | 3/2002 | Konfino et al. |
| 2006/0172942 A1 | 8/2006 | Dolitzky |
| 2007/0021341 A1* | 1/2007 | Sela et al. ................ 514/12 |
| 2008/0021192 A1* | 1/2008 | Iyer et al. ................ 528/314 |

FOREIGN PATENT DOCUMENTS

| | | |
|---|---|---|
| WO | WO 00/50250 | 8/2000 |
| WO | WO 2004/043995 | 5/2004 |
| WO | WO 2006/029411 | 3/2006 |
| WO | WO 2007/022193 | 2/2007 |
| WO | WO 2007/030573 | 3/2007 |

OTHER PUBLICATIONS

Teitelbaum et al. "Suppression of experimental allergic encephalomyelitis by a synthetic polypeptide." *Eur. J. Immunol. Vol. 1.* 1971. pp. 242-248.

* cited by examiner

*Primary Examiner* — Jeffrey S. Lundgren
*Assistant Examiner* — William Lee
(74) *Attorney, Agent, or Firm* — Merchant & Gould P.C.

(57) ABSTRACT

This invention relates to a convenient and improved process for preparation of glatiramer acetate (copolymer-1) of pharmaceutical grade. The process involves polymerizing N-carboxyanhydrides of tyrosine, alanine, γ-benzyl glutamate and ε-N-trifluoroacetyllysine in dioxane with diethylamine as initiator to afford protected copolymer-1. Treatment with hydrogen bromide in acetic acid at 35° C. for 3-5 h cleaves benzyl group to produce trifluoroacetyl copolymer-1. The trifluoroacetyl copolymer-1 is washed with an organic solvent to remove reactive benzyl bromide generated during debenzylation. Deprotection with aqueous piperidine, followed by dialysis offers glatiramer acetate (copolymer-1) of Molecular weight 5000-9000 daltons.

5 Claims, 4 Drawing Sheets

1

PROCESS FOR THE PREPARATION GLATIRAMER ACETATE (COPOLYMER-1)

This application is a National Stage Application of PCT/IN2007/000432, filed 24 Sep. 2007, which claims benefit of Serial No. 1673/CHE/2007, filed 31 Jul. 2007 in India and which applications are incorporated herein by reference. To the extent appropriate, a claim of priority is made to each of the above disclosed applications.

BACKGROUND OF THE INVENTION

Glatiramer acetate is one of the important drugs for the treatment of Remitting and Relapsing form of Multiple Sclerosis (RRMS). It belongs to a unique chemical class of compounds known as polypeptides or peptide polymers. Glatiramer acetate is also known as copolymer-1. It is a copolymer comprising of four naturally occurring amino acids namely L-glutamic acid, L-alanine, L-tyrosine and L-lysine with an approximate average molar fraction of 0.141, 0.427, 0.095 and 0.338 and an average molecular weight of 5000-9000 daltons.

The process for preparation of glatiramer acetate is described in Euro. J. Immune. 1, 242 (1971) [Tietelbaum et al.], U.S. Pat. No. 3,849,550 [Tietelbaum, et al.]. In these publications, the process reported consists of polymerizing N-carboxyanhydrides of tyrosine, alanine, γ-benzyl glutamate and ε-N-trifluoroacetyllysine in dioxane with diethylamine as initiator to afford protected copolymer-1. The deblocking of γ-carboxyl group of glutamic acid in the protected copolymer-1 is affected by hydrogen bromide in acetic acid to yield trifluoroacetyl copolymer-1. Removal of trifluoroacetyl group of lysine from trifluoroacetyl copolymer-1 by aqueous piperidine, followed by dialysis yields copolymer-1 (glatiramer acetate). In addition U.S. Pat. No. 5,800,808; U.S. Pat. No. 5,981,589; U.S. Pat. No. 6,048,898; U.S. Pat. No. 6,054,430; U.S. Pat. No. 6,342,476; U.S. Pat. No. 6,362,161 and WO 00/05250, also describe essentially the same method for preparation of glatiramer acetate. These patents elaborate on the process indicated in the earlier patents cited above, like specifying the debenzylation reaction time of protected copolymer-1. As per these patents, the debenzylation reaction is carried out for 10-50 h at 20-28° C. to achieve the molecular weight of 5000-9000 daltons for glatiramer acetate.

Indian patent IP 190759 claims the method of manufacturing of copolymer-1. This patent also claims as in the above cited US patents the conditions for the debenzylation step. The debenzylation reaction is carried out for 10-50 h at 20-28° C. to achieve the desired molecular weight of 5000-9000 daltons for glatiramer acetate.

The debenzylation reaction with hydrogen bromide in acetic acid is hazardous on account of release of hydrogen bromide fumes. In addition, benzyl bromide is generated as reaction by-product. The released benzyl bromide is a highly reactive electrophile and reacts with nucleophiles like primary and secondary amines to generate unwanted N-alkylated products. Also, it is highly lachrymatory and handling it in large quantities on commercial scale is hazardous and unsafe. None of the above patents provide a method for removing benzyl bromide impurity from the reaction mixtures. The present invention describes debenzylation reaction of protected copolymer-1 for shorter duration of time at a higher temperature and a method to remove benzyl bromide from the reaction mixture.

According to WO 2004/043995, glatiramer acetate is prepared employing building blocks N-carboxyanhydrides of L-,γ-benzyl glutamate, ε-N-benzyllysine, alanine, and tyrosine. In this patent the benzyl protecting groups are deblocked by palladium carbon in a single stage. In the US patent 2006/00172942 A1, benzyl deprotection by hydrogenolysis is described. Both these methods use building blocks those are difficult to prepare and are not available in commercial quantities.

SUMMARY OF THE INVENTION

The main purpose of present of invention is to prepare glatiramer acetate of pharmaceutical grade with an average molecular weight distribution of 5000-9000 daltons. The process consists of polymerizing N-carboxyanhydrides of tyrosine, alanine, γ-benzyl glutamate and ε-N-trifluoroacetyllysine in dioxane with diethylamine as initiator to give protected copolymer-1. Deblocking of γ-carboxyl group of glutamic acid by hydrogen bromide in acetic acid is carried out at 35-45° C. for 1-5 h to get trifluoroacetyl copolymer-1.

Removal of reactive benzyl bromide generated as byproduct in the reaction is achieved by washing the intermediate trifluoroacetyl copolymer-1 with an organic solvent. Cleaving trifluoroacetyl group from lysine residue by aqueous piperidine yields glatiramer acetate.

The main objective of invention is to prepare glatiramer acetate of pharmaceutical grade with 5000-9000 daltons average molecular weight by a process, which is simple, convenient and non-hazardous.

The objective of invention is to prepare trifluoroacetyl copolymer-1 an intermediate used in the preparation glatiramer acetate.

Another objective of the invention is to prepare trifluoroacetyl copolymer-1 by a process, which involves treating with hydrogen bromide in acetic acid to affect debenzylation of, protected copolymer-1.

Still another objective of the present invention is to prepare trifluoroacetyl copolymer-1 by treating hydrogen bromide in acetic acid to affect debenzylation of protected copolymer-1 for shorter reaction time for safety reasons.

Yet another objective of this invention is to wash the intermediate trifluoroacetyl copolymer-1 with an organic solvent to render the product free of hazardous and reactive benzyl bromide.

Still, yet another objective of present invention is to prepare trifluoroacetyl copolymer-1, by treating hydrogen bromide in acetic acid to affect debenzylation of protected copolymer-1 for shorter duration of time, during 1-5 h at 35-45° C. and washing with an organic solvent such as diisopropyl ether, diethyl ether, ethyl acetate to remove reactive and hazardous benzyl bromide.

DETAILED DESCRIPTION OF THE INVENTION

The present of invention describes a method to prepare glatiramer acetate (copolymer 1) of pharmaceutical grades with an average molecular weight of 5000-9000 daltons. The process consists of polymerizing N-carboxyanhydrides of tyrosine, alanine, γ-benzyl glutamate and ε-N-trifluoroacetyllysine in dioxane with diethylamine as initiator to give protected copolymer-1. In the protected copolymer-1, γ-carboxyl group of glutamic acid is protected by benzyl group and ε-amine function of lysine by trifluoroacetyl group. Treatment of protected copolymer-1 with hydrogen bromide in acetic acid produces trifluoroacetyl copolymer-1. Removal of trifluoroacetyl group of lysine in trifluoroacetyl copolymer-1 by aqueous piperidine yields glatiramer acetate (copolymer-1).

Removal of benzyl protection group of glutamic acid is affected by 33% hydrogen bromide in acetic acid. This reaction is done at 20-28° C. for 10-50 h in the prior art. Hydrogen bromide is corrosive and its fumes are hazardous. Hence it creates safety problem in an industrial set-up. During the debenzylation reaction, highly reactive benzyl bromide is formed as by-product. It is not only lachrymatory but also highly reactive and readily alkylates free amino groups present at the N terminal end of polymer chains. Keeping the above issues in view, attempts are made to modify the process. Firstly the reactions are conducted at 35-45° C. for 1-5 h to reduce the reaction time. Secondly, in order to eliminate benzyl bromide, the filtered product is washed with an organic solvent. The organic solvent is so chosen that the desired product remains insoluble and the unwanted benzyl bromide by-product is washed away in the soluble portion.

The most preferable conditions are reaction time of 3 h at 35° C. The preferable solvents to wash the intermediate product are ethers such as diisopropyl, and diethyl ether. The copolymer-1 (glatiramer acetate) obtained under these conditions and after deacetylation and dialysis shows an average molecular weight of 5000-9000 daltons with required amino acid ratios.

Figure 1:
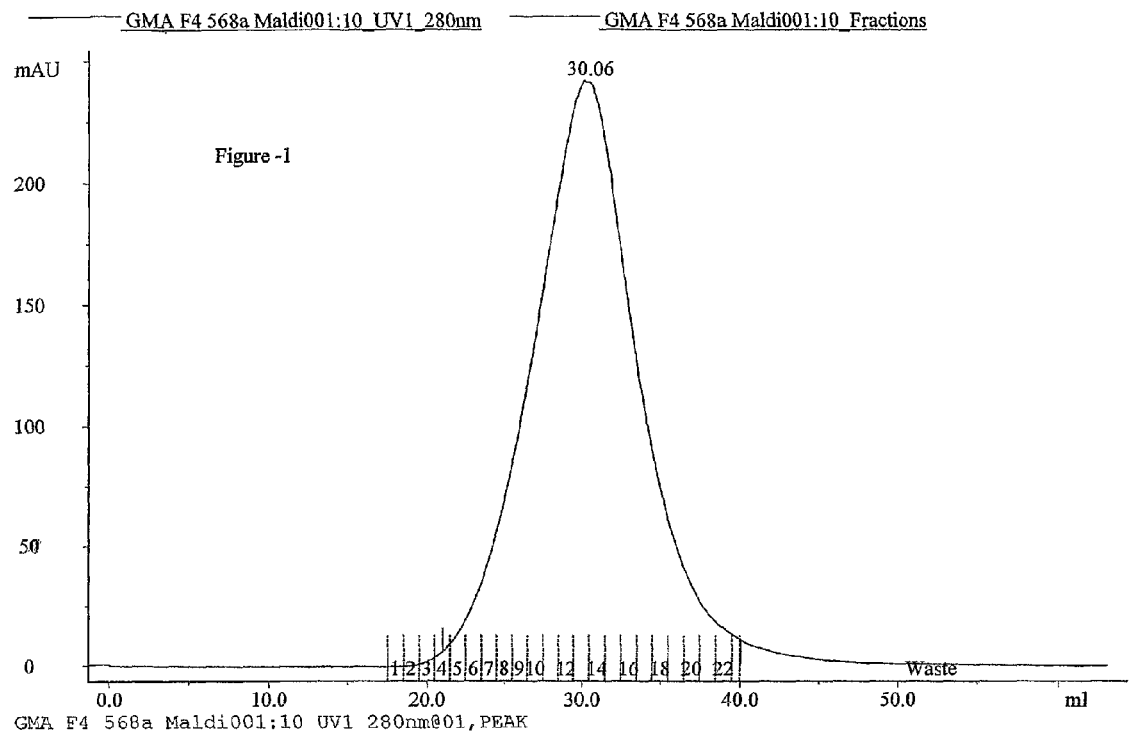
FIG. 1: Size exclusion chromatogram of glatiramer acetate prepared as per Example-1
Figure 2:
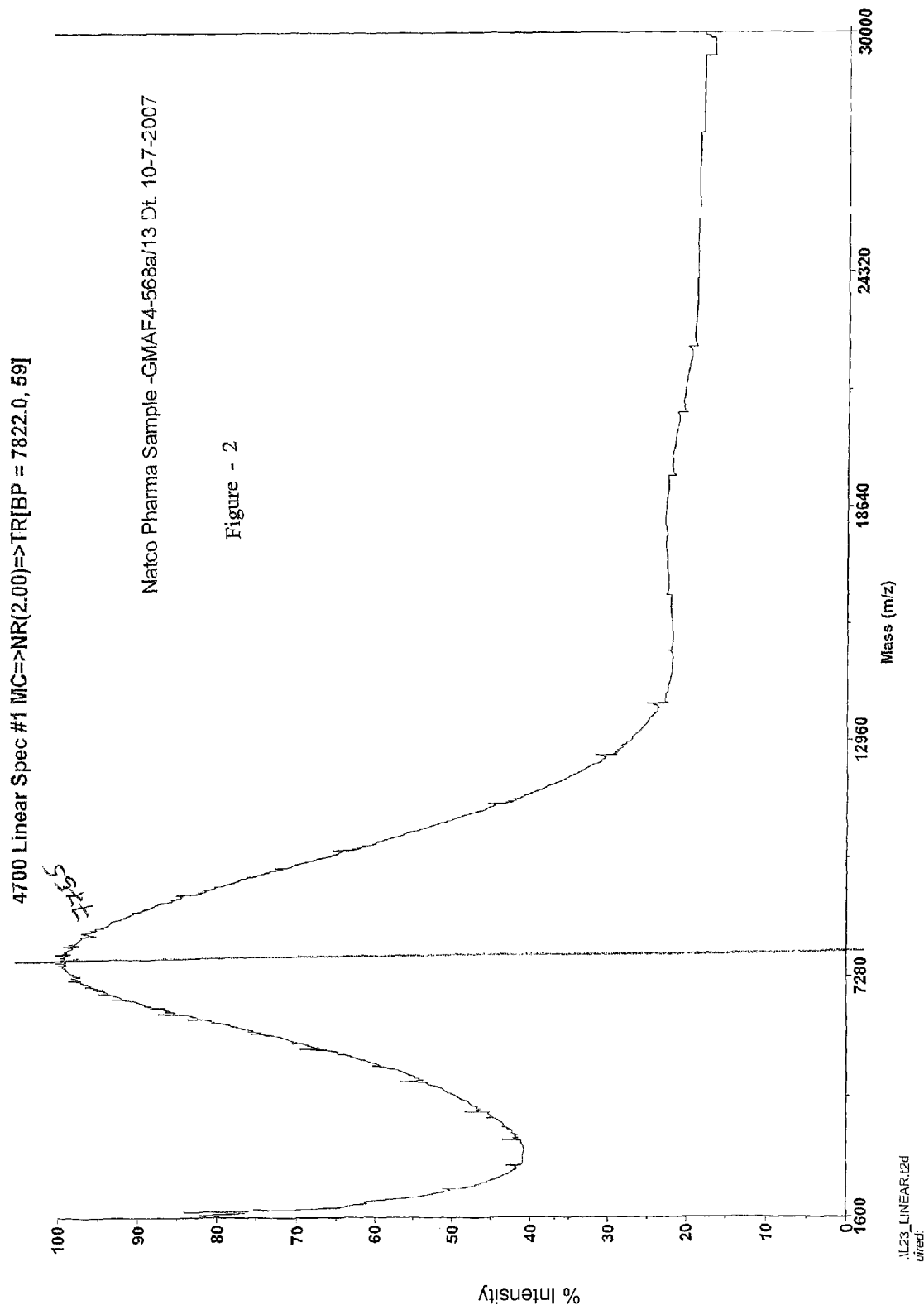
FIG. 2: SEC/MALDI spectrum of glatiramer acetate prepared as per Example-1.
Figure 3:
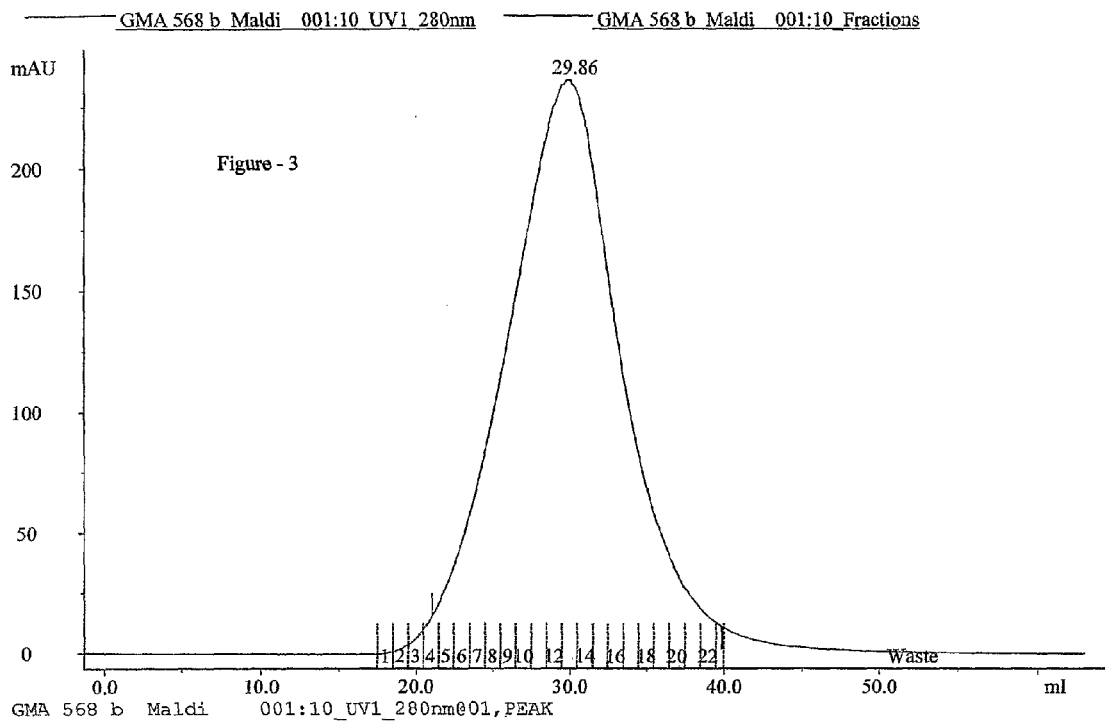
FIG. 3: Size exclusion chromatogram of glatiramer acetate prepared as per Example-2
Figure 4:
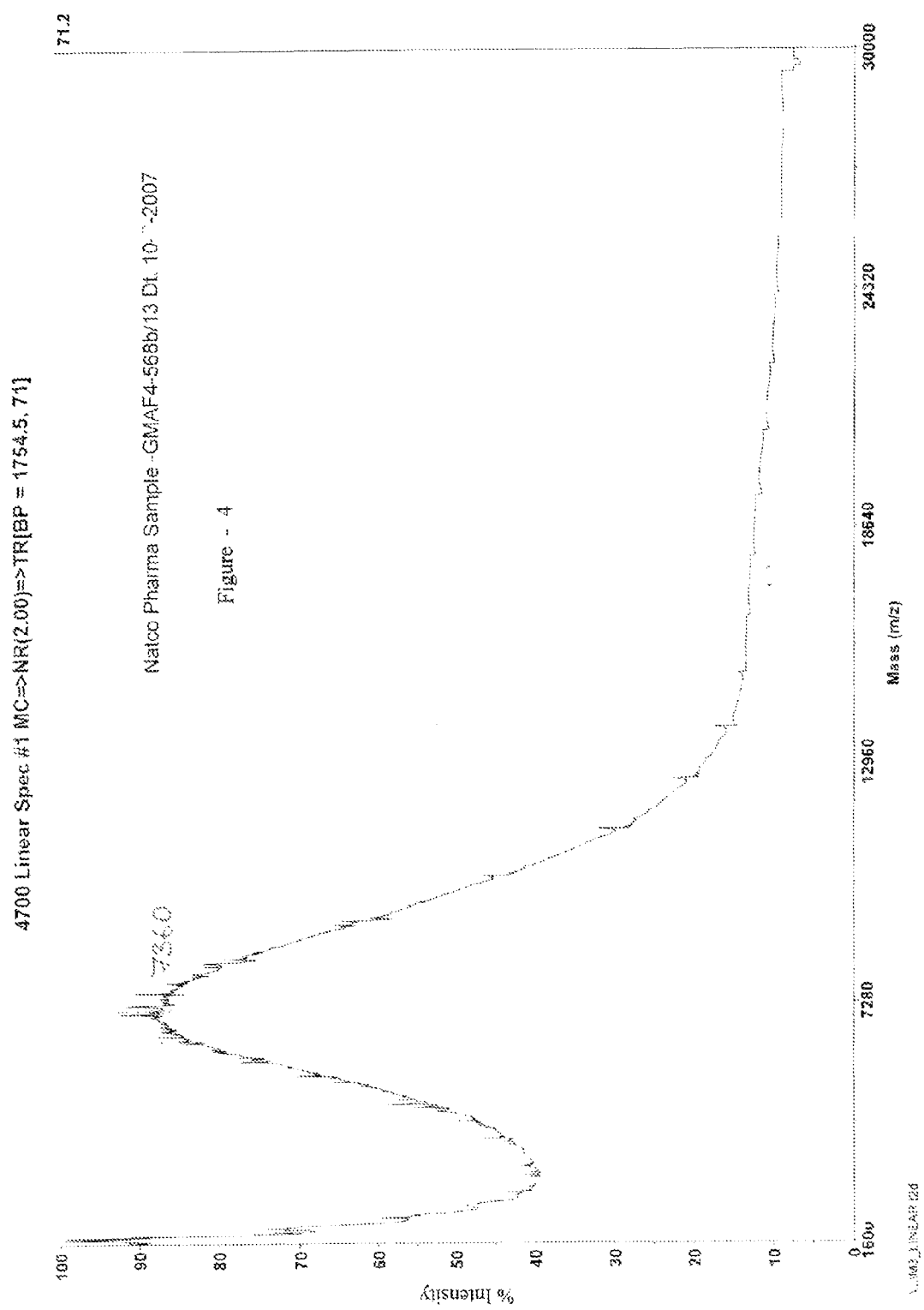
FIG. 4: SEC/MALDI spectrum of glatiramer acetate prepared as per Example-2

Size exclusion chromatogram and molecular weight by SEC/MALDI spectrum are shown in FIGS. 1-4.

EXAMPLE 1

(a) Preparation of Protected Copolymer-1

Protected copolymer-1 is prepared as described by Tietelbaum et al. in Eur. J. Immune. Vol. 1, 242 (1971). N-carboxyanhydrides of tyrosine (130 g), alanine (360 g), γ-benzyl glutamate (250 g) and ε-N-trifluoroacetyllysine (595 g) are dissolved in dioxane (30 L). To this diethyl amine (3.6 mL) is added to initiate polymerization. The reaction mixture is stirred at 25'C for 24 h and poured into water (200 L). The precipitated product is filtered, washed with water (50 L) and dried. Yield: 950 g

(b) Preparation of Trifluoroacetyl Copolymer-1

Protected copolymer-1 (50 g) is treated with 33% hydrogen bromide in acetic acid (550 mL) and stirred at 35° C. for 3 h. Then the reaction mixture is poured into ice cold water (10 L). Precipitated product is filtered and washed with cold water (2.5 L).

Removal of Benzyl Bromide.

The filtered product is treated with diisopropyl ether (2×1.5 L), stirred for 15-20 min and filtered. The washed product is dried at 40° C. under vacuum for 12 h. Yield: 37 g (moisture content is <0.5%).

(c) Preparation of Copolymer-1

Trifluoroacetyl copolymer-1 (30 g) is treated with 10% solution of piperidine in water and stirred for 24 h at 25° C. The solution is dialyzed first in water till pH 8-9 then in 0.4% acetic acid till pH 5.5 is achieved. The solution is lyophilized to a get fluffy yellow product. Yield: (18 g)

Amino acid ratio: Tyrosine: 0.093; Alanine: 0.420; Lysine 0.347; glutamic acid: 0.140

Molecular weight by SEC/MALDI: 7755 daltons

EXAMPLE 2

(a) Preparation of Protected Copolymer-1

Protected copolymer-1 is prepared as described by Tietelbaum et al. In Eur. J. Immune. Vol. 1, 242 (1971). N-carboxyanhydrides of tyrosine (130 g), alanine (360 g), γ-benzyl glutamate (250 g) and ε-N-trifluoroacetyllysine (595 g) are dissolved in dioxane (30 L). To this diethyl amine (3.6 mL) is added to initiate polymerization. The reaction mixture is stirred at 25° C. for 24 h and poured into water (200 L). The precipitated product is filtered, washed with water (50 L) and dried. Yield: 930 g

(b) Preparation of Trifluoroacetyl Copolymer-1

Protected copolymer-1 (50 g) is treated with 33% hydrogen bromide in acetic acid (550 mL) and stirred at 40° C. for 2 h. Then the reaction mixture is poured into ice cold water (10 L). Precipitated product is filtered and washed with cold water (2.5 L).

Removal of Benzyl Bromide.

The filtered product is treated with ethylacetate (2×1.5 L), stirred for 15-20 min and filtered. The washed product is dried at 40° C. under vacuum for 12 h. Yield: 34 g (moisture content is <0.5%)

(c) Preparation of Copolymer-1

Trifluoroacetyl copolymer-1 (30 g) is treated with 10% solution of piperidine in water and stirred for 24 h at 25° C. The solution is dialyzed first in water till pH 8-9 then in 0.4% acetic acid till pH 5.5 is achieved. The solution is lyophilized to a get fluffy yellow product. Yield: (20 g)

Amino acid ratio: Tyrosine: 0.098; Alanine: 0.435; Lysine 0.343; glutamic acid: 0.141 Molecular weight by SEC/MALDI: 7360 daltons

The invention claimed is:

1. A process for preparing copolymer-1, comprising:
reacting protected copolymer-1 with hydrobromic acid for 1 to 5 hr at 35-45° C. to form trifluoroacetyl copolymer-1;
washing the trifluoroacetyl copolymer-1 with organic solvent, thus removing benzyl bromide, wherein the organic solvent comprises a hydrocarbon, a halogenated hydrocarbon, an alcohol, an ether, or an ester;
treating the trifluoroacetyl copolymer-1 with aqueous piperidine to form copolymer-1; and
purifying the copolymer-1;
wherein copolymer-1 has a molecular weight of 5,000 to 9,000 Daltons and is glatiramer acetate comprising a mixture of polypeptides composed of glutamic acid, alanine, tyrosine, and lysine in a molar ratio of approximately of 0.141, 0.427, 0.095 and 0.338.

2. The method of claim 1, comprising reacting the protected copolymer 1 with hydrobromic acid for 3 hr at 35-45° C.

3. The method of claim 1, wherein the organic solvent comprises diisopropyl ether, diethyl ether, or ethyl acetate.

4. A process for preparing copolymer-1, comprising:
reacting protected copolymer-1 with hydrobromic acid for 1 to 5 hr at 35-45° C. to form trifluoroacetyl copolymer-1;
washing the trifluoroacetyl copolymer-1 with diisopropyl ether, diethyl ether, or ethyl acetate, thus removing benzyl bromide;
treating the trifluoroacetyl copolymer-1 with aqueous piperidine to form copolymer-1; and
purifying the copolymer-1;
wherein copolymer-1 has a molecular weight of 5,000 to 9,000 Daltons and is glatiramer acetate comprising a mixture of polypeptides composed of glutamic acid, alanine, tyrosine, and lysine in a molar ratio of approximately of 0.141, 0.427, 0.095 and 0.338.

5. The method of claim 4, comprising reacting the protected copolymer 1 with hydrobromic acid for 3 hr at 35-45° C.

* * * * *